United States Patent [19]

Nakai et al.

[11] Patent Number: 5,514,713
[45] Date of Patent: May 7, 1996

[54] AMIDINOPHENOL DERIVATIVES

[75] Inventors: Hisao Nakai; Koumei Kamiyasu; Masanori Kawamura, all of Mishima, Japan

[73] Assignee: Ono Pharmaceutical Co., Ltd., Osaka, Japan

[21] Appl. No.: 352,723

[22] Filed: Dec. 2, 1994

[30] Foreign Application Priority Data

Dec. 3, 1993 [JP] Japan .................................. 5-304048

[51] Int. Cl.$^6$ ............................................. A61K 31/235
[52] U.S. Cl. ............................. 514/533; 560/35; 560/42
[58] Field of Search ........................ 560/35, 42; 514/533

[56] References Cited

U.S. PATENT DOCUMENTS

| | | |
|---|---|---|
| 2,868,691 | 1/1959 | Porush et al. . |
| 3,095,355 | 6/1963 | Abramson et al. . |
| 4,514,416 | 4/1985 | Fuji et al. . |
| 4,570,006 | 2/1986 | Fuji et al. . |

Primary Examiner—José G. Dees
Assistant Examiner—Samuel Barts
Attorney, Agent, or Firm—Watson Cole Stevens Davis

[57] ABSTRACT

Disclosed are amidinophenol derivatives of the formula (I) and acid-addition salts thereof (in which $R^1$ and $R^2$ are alkyl, alkoxy, acyl, halogen, nitro, benzoyl, $COOR_4$; A is bond, alkylene, group of the formula (II); $R^3$ is group of the formula (III), (IV))

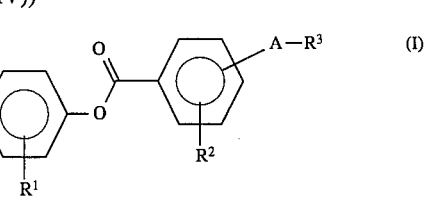

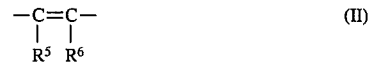

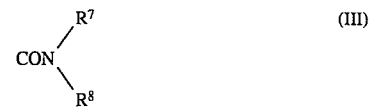

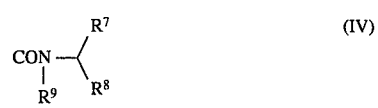

Compounds of the formula (I) have inhibitory activities on phospholipase $A_2$ and proteases (especially trypsin), and are useful for the prevention and/or the treatment of inflammatory diseases, allergic diseases, disseminated intravascular coagulation, pancreatitis, severity in pancreatitis and multiple organ failure.

12 Claims, No Drawings

AMIDINOPHENOL DERIVATIVES

FIELD OF THE INVENTION

The present invention relates to amidinophenol derivatives, processes for preparation thereof and pharmaceutical compositions containing these amidinophenol derivatives.

BACKGROUND OF THE INVENTION

Phospholipase $A_2$ ($PLA_2$) is an enzyme which acts on phospholipids existing in cell membrane and hydrolyzes an ester bond at the second position of the phospholipids. There are known two kinds of $PLA_2$, i.e., membrane-associated $PLA_2$ and pancreatic $PLA_2$.

Membrane-associated $PLA_2$ acts on phospholipids to release arachidonic acid (AA) from the phospholipids. The AA is converted into prostaglandins, thromboxanes and leukotrienes, which are physiologically active substances inducing various inflammatory diseases and allergic diseases.

On the other hand, pancreatic $PLA_2$ degrades phosphoric acid and destroys cell membrane, thereby to produce lysolecithin having strong cytotoxicity. Recently, much importance has been attached to pancreatitis, severity in pancreatitis and multiple organ failure induced by such destructive activity on cell membrane. Further, it is reported that membrane-associated $PLA_2$ is also concerned with these diseases.

Accordingly, the inhibition on $PLA_2$ leads to the suppression of the release of AA, a precursor of various physiologically active substances, and therefore, it is considered to be useful for the prevention and/or the treatment of various inflammatory and allergic diseases. Furthermore, it is considered to be useful for the prevention and/or the treatment of pancreatitis, severity in pancreatitis and multiple organ failure due to the inhibition of destructive activity on cell membrane.

RELATED ARTS

Many compounds having an inhibitory activity on $PLA_2$ are known. For example, there are known, as guanidino containing compounds, guanidinobenzoic acid derivatives such as camostat mesylate (code No. FOY-305) of the formula (X):

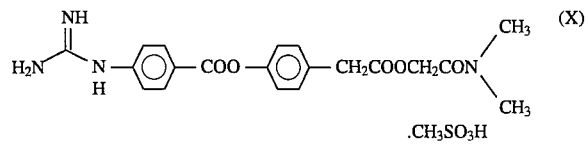

.$CH_3SO_3H$ and nafamostat mesylate (code No. FUT-175) of the formula (Y):

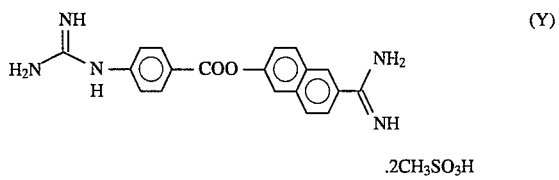

.$2CH_3SO_3H$ (see Japanese Journal of Clinical Medicine, 48 (1), 165–172, 1990).

Further, there is known as a compound having a chemical structure partially similar to ones of the present invention, compounds of the formula (Z):

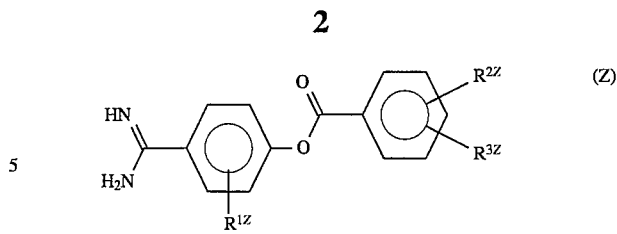

where in $R^{1Z}$ is:
(i) C1–4 alkyl,
(ii) C1–4 alkoxy,
(iii) carboxy,
(iv) $COOR^{4Z}$ (in which $R^{4Z}$ is C1–4 alkyl),
(v) halogen,
(vi) nitro,
(vii) sulfo,
(viii) benzoyl, or
(ix)

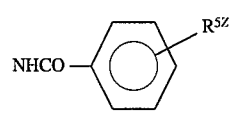

(in which $R^{5Z}$ is hydrogen or guanidino);
$R^{2Z}$ and $R^{3Z}$ each, independently, is:
(i) NHCO—$R^{6Z}$ (in which $R^{6Z}$ is C1–4 alkyl), or
(ii)

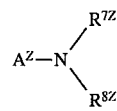

(in which $A^Z$ is bond, methylene or ethylene;
$R^{7Z}$ and $R^{8Z}$ each, independently, is
(1) hydrogen,
(2) C1–4 alkyl, or
(3) amino-protecting group (it refers to
 [1] $COOR^{9Z}$ (in which $R^{9Z}$ is t-butyl or benzyl),
 [2] acetyl,
 [3] benzoyl,
 [4] tosyl, or
 [5] nitro););
(definitions not related are omitted) (see the specification of U.S. Pat. Nos. 4,514,416 and 4,570,006). In these specifications, it is disclosed that the compounds have an inhibitory activity on protease such as trypsin, plasmin, and anti-complement effect, but it is not described that the compounds have an inhibitory activity on $PLA_2$.

OBJECTS OF THE INVENTION

An object of the present invention is to find novel compounds possessing an inhibitory activity on $PLA_2$. As the result of energetic investigations, the present inventors have found that the object is accomplished by the amidinophenol derivatives of the formula (I) below.

Another object of the present invention is to provide compounds possessing a strong inhibitory activity on various proteases such as trypsin, plasmin, thrombin, kallikrein, especially trypsin.

SUMMARY OF THE INVENTION

The present invention relates to amidinophenol derivatives.

More particularly, it relates to:
(i) amidinophenol derivatives of the formula (I):

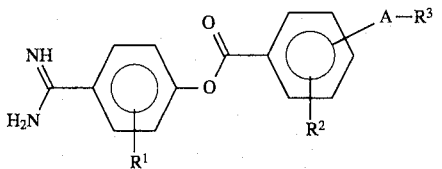

(wherein the various symbols are the same meaning hereafter described) and acid-addition salts thereof, having an inhibitory activity on phospholipase $A_2$ ($PLA_2$) and on various proteases, especially trypsin,
(ii) processes for the preparation thereof, and
(iii) pharmaceutical agents containing them.

COMPARISON WITH THE RELATED ARTS

The amidinophenol derivatives of the present invention have never been known before, and, therefore, are quite novel.

To summarize, $R^{2z}$ and $R^{3z}$ in the formula (Z) hereinbefore depicted can represent NHCO—$R^{6z}$, but the nitrogen atom in the group is attached directly to a benzene ring, and further $R^{6z}$ represents only an alkyl group. On the other hand, $R^3$ in the compounds of the present invention represents CON($R^7$)($R^8$) or CON($R^9$)—CH($R^7$)($R^8$); but in any case, the carbon atom in the group is attached to a benzene ring via a group of A.

From the above viewpoint, it can be said that the compounds of the present invention have the chemical structure quite different from the compounds of the formula (Z).

Furthermore, it has never been known that amidinophenol derivatives (compounds of the formulae (Z) hereinbefore depicted) have an inhibitory activity on $PLA_2$, though some guamidinobenzoic acid derivatives (compounds of the formulae (X) and (Y) hereinbefore depicted) have already been known to have the activity.

Accordingly, it is quite unexpected from the related arts, that the amidinophenol derivatives of the present invention have an inhibitory activity on $PLA_2$.

DETAILED DESCRIPTION OF THE INVENTION

The present invention relates to:
1) compounds of the formula (I):

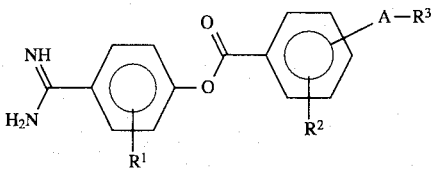

where in $R^1$ and $R^2$ each, independently, is:
(i) hydrogen,
(ii) C1–4 alkyl,
(iii) C1–4 alkoxy,
(iv) C2–5 acyl,
(v) halogen,
(vi) nitro,
(vii) benzoyl, or
(viii) COOR$^4$ (in which R$^4$ is C1–3 alkyl);

A is bond, C1–4 alkylene or

(in which $R^5$ and $R^6$ each, independently, is hydrogen or C1–4 alkyl); $R^3$ is

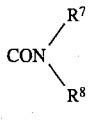 (i)

or

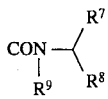 (ii)

(in which $R^7$ and $R^8$ each, independently, is
(1) hydrogen,
(2) phenyl,
(3) C7–10 phenylalkyl,
(4) phenyl or C7–10 phenylalkyl each of which is substituted by one or two substituents selected from C1–4 alkyl, halogen and $R^{11}$—COOR$^{12}$ (in which $R^{11}$ is
[1] bond,
[2] C1–8 alkylene,
[3] C2–8 alkenylene, or
[4] C2–8 alkynylene;
$R^{12}$ is
1] hydrogen,
2] C1–4 alkyl,
3] C7–10 phenylalkyl,
4] phenyl,
5] allyl (i.e., —$CH_2$—CH=$CH_2$), or
6] propargyl (i.e., —$CH_2$—C≡CH)),
(5) C1–10 alkyl,
(6) C2–10 alkenyl having one to three double bonds,
(7) C2–10 alkynyl having one or two triple bonds,
(8) $R^{11a}$—COXR$^{12}$
(in which $R^{11a}$
[1] bond,
[2] C1–8 alkylene,
[3] C2–8 alkylene in which one or two carbon atoms in the main chain are replaced by sulfur, or sulfur and phenylene,
[4] C2–8 alkenylene,
[5] C4–8 alkenylene in which one or two carbon atoms in the main chain are replaced by sulfur, or sulfur and phenylene,
[6] C2–8 alkynylene, or
[7] C4–8 alkynylene in which one or two carbon atoms in the main chain are replaced by sulfur, or sulfur and phenylene,
X is oxygen or —NH—, and $R^{12}$ is the same meaning as hereinbefore defined),
(9) C1–4 alkyl which is substituted by a 7–14 membered, bi- or tri-cyclic hetero ring containing one nitrogen,
(10) C3–7 cycloalkyl, or
(11) C1–6 alkyl which is substituted by C1–4 alkoxy;
$R^9$ is
(1) hydrogen,
(2) C1–8 alkyl,
(3) C7–10 phenylalkyl, (4) C2–10 alkenyl having one to three double bonds,
(5) C2–10 alkynyl having one or two triple bonds,
(6) $R^{11}$—$COOR^{12}$ (in which $R^{11}$ and $R^{12}$ are the same meaning as herein before defined),
(7) C3–7 cycloalkyl, or
(8) C1–6 alkyl which is substituted by C1–4 alkoxy); with the proviso that
(i) at least one group in $R^7$, $R^8$ and $R^9$ represents C1–6 alkyl which is substituted by C1–4 alkoxy,
(ii) both $R^7$ and $R^8$ do not represent hydrogen at the same time, and
(iii) when at least one group in $R^7$, $R^8$ and $R^9$ represents groups containing t-butyl ester, the other groups do not represent groups containing carboxy; or acid-addition salts thereof;

2) processes for the preparation thereof, and 3) pharmaceutical agents containing them as active ingredient.

It will be understood that formula (i) and (ii) may overlap. Formula (ii) should be construed as excluding groupings already embraced by formula (i).

Throughout the specification including claims, it may be easily understood by those skilled in the art, that all isomers are included in the present invention. For example, the alkyl, alkoxy, alkylene, alkenylene and alkynylene groups include straight-chain and also branched-chain ones, and the double bonds in the alkenylene group include E, Z and EZ mixture. Accordingly, all isomers produced by the existence of asymmetric carbon atoms are included in the present invention when branched-chain alkyl, alkoxy, alkylene, alkenylene, alkynylene etc. exist.

In the formula (I), the C1–4 alkyl group represented by $R^1$, $R^2$, $R^5$, $R^6$ and $R^{12}$, and that in $R^7$ and $R^8$, means methyl, ethyl, propyl, butyl and the isomers thereof.

In the formula (I), the C1–4 alkoxy group represented by $R^1$ and $R^2$, means methoxy, ethoxy, propoxy, butoxy and the isomers thereof.

In the formula (I), the C1–3 alkyl group represented by $R^4$, means methyl, ethyl, propyl and the isomers thereof.

In the formula (I), the C2–5 acyl group represented by $R^1$ and $R^2$, means acetyl, propionyl, butyryl, valeryl and the isomers thereof.

In the formula (I), the C1–10 alkyl group represented by $R^7$ and $R^8$, means methyl, ethyl, propyl, butyl, pentyl, hexyl, heptyl, octyl, nonyl, decyl and the isomers thereof.

In the formula (I), the C1–8 alkyl group represented by $R^9$, means methyl, ethyl, propyl, butyl, pentyl, hexyl, heptyl, octyl and the isomers thereof.

In the formula (I), the C7–10 phenylalkyl group represented by $R^7$, $R^8$, $R^9$ and $R^{12}$, means methyl, ethyl, propyl, butyl and the isomers thereof, which are substituted by a phenyl group.

In the formula (I), the halogen atom represented by $R^1$ and $R^2$, and that in $R^7$ and $R^8$, mean fluorine, chlorine, bromine and iodine atoms.

In the formula (I), the C1–4 alkylene group represented by A, means methylene, ethylene, trimethylene, tetramethylene and the isomers thereof.

In the formula (I), the C1–8 alkylene group represented by $R^{11}$ and $R^{11a}$, means methylene, ethylene, trimethylene, tetramethylene, pentamethylene, hexamethylene, heptamethylene, octamethylene and the isomers thereof. The C2–8 alkenylene group means vinylene, propenylene, butenylene, pentenylene, hexenylene, heptenylene, octenylene and the isomers thereof. The C2–8 alkynylene group means ethynylene, propynylene, butynylene, pentynylene, hexynylene, heptynylene, octynylene and the isomers thereof.

In the formula (I), the C2–8 alkylene in which carbon atoms in the main chain are replaced by sulfur, or sulfur and phenylene, represented by $R^{11a}$, means thiaethylene (i.e., —$CH_2$—S— and —S—$CH_2$—), thiatrimethylene (i.e., —$CH_2$—$CH_2$—S—, —$CH_2$—S—$CH_2$—, —S—$CH_2$—$CH_2$—), thiatetramethylene, thiapentamethylene, thiahexamethylene, thiaheptamethylene, thiaoctamethylene and the isomers thereof, or the group in which one of any methylene group in the said thiaalkylene group, is replaced by a phenylene group (e.g., —$CH_2$—S—$CH_2$—$C_6H_4$—).

The C4–8 alkenylene in which carbon atoms in the main chain are replaced by sulfur, or sulfur and phenylene, means thiabutenylene (e.g., —S—$CH_2$—CH=CH— and —CH=CH—$CH_2$—S—), thiapentenylene (e.g., —S—$CH_2$—$CH_2$—CH=CH—, —S—$CH_2$—CH=CH—$CH_2$— and —$CH_2$—S—$CH_2$—CH=CH—), thiahexenylene, thiaheptenylene, thiaoctenylene and the isomers thereof, or the group in which one of any methylene group in the said thiaalkenylene group, is replaced by a phenylene group (e.g., —S—$CH_2$—CH=CH—$C_6H_4$—).

The C4–8 alkynylene in which carbon atoms in the main chain are replaced by sulfur, or sulfur and phenylene, means thiabutynylene (e.g., —S—$CH_2$—C≡C—), thiapentynylene (e.g., —S—$CH_2$—$CH_2$—C≡C—, —S—$CH_2$—C≡C—$CH_2$— and —$CH_2$—S—$CH_2$—C≡C—), thiahexynylene, thiaheptynylene, thiaoctynylene and the isomers thereof, or the group in which one of any methylene groups in the said thiaalkynylene group, is replaced by a phenylene group (e.g., —S—$CH_2$—C≡C—$C_6H_4$—).

In the formula (I), examples of the 7–14 membered, bi- or tri-cyclic hetero ring containing one nitrogen, in $R^7$ and $R^8$, are indole, indoline, quinoline, 1,2,3,4-tetrahydroquinoline, carbazole, etc.

In the formula (I), the C2–10 alkenyl having one to three double bonds, represented by $R^7$, $R^8$ and $R^9$, means ethenyl, propenyl, butenyl, pentenyl, hexenyl, heptenyl, octenyl, nonenyl, decenyl, butadienyl, pentadienyl, hexadienyl, heptadienyl, octadienyl, nonadienyl, decadienyl, hexatrienyl, heptatrienyl, octatrienyl, nonatrienyl, decatrienyl and the isomers thereof. The C2–10 alkynyl having one or two triple bonds, means ethynyl, propynyl, butynyl, pentynyl, hexynyl, heptynyl, octynyl, nonynyl, decynyl, butadiynyl, pentadiynyl, hexadiynyl, heptadiynyl, octadiynyl, nonadiynyl, decadiynyl and the isomers thereof.

In the formula (I), the cycloalkyl group represented by $R^7$, $R^8$ and $R^9$, means cyclopropyl, cyclobutyl, cyclopentyl, cyclohexyl and cycloheptyl.

In the formula (I), the C1–6 alkyl substituted by C1–4 alkoxy represented by $R^7$, $R^8$ and $R^9$, means methyl, ethyl, propyl, butyl, pentyl, hexyl and the isomers thereof, which are substituted by methoxy, ethoxy, propoxy, butoxy and the isomers thereof.

In the compounds of the present invention, the compounds of the formula (I-A) are preferably.

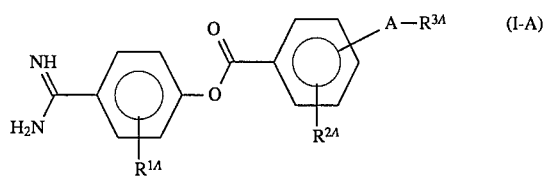

wherein $R^{1A}$ and $R^{2A}$ are the same meaning as hereinbefore defined for $R^1$ and $R^2$ respectively $R^{3A}$ $$\text{CON} \begin{matrix} R^{7A} \\ | \\ R^{8A} \end{matrix} \quad \text{(i)}$$

or $$\text{CON} \begin{matrix} R^{7A} \\ | \\ R^{9A} \end{matrix} R^{8A} \quad \text{(ii)}$$

(in which $R^{7A}$ and $R^{8A}$ each, independently, is
(1) phenyl or C7–10 phenylalkyl each of which is substituted by one or two substituents by $R^{11}$—COOR$^{12}$ (wherein $R^{11}$ and $R^{12}$ are the same meanings as hereinbefore defined),
(2) $R^{11a}$—COXR$^{12}$ (wherein $R^{11a}$, $R^{12}$ and X are the same meanings as hereinbefore defined), or
(3) C1–6 alkyl which is substituted by C1–4 alkoxy; $R^{9A}$ is
(1) hydrogen,
(2) $R^{11}$—COOR$^{12}$ (wherein $R^{11}$ and $R^{12}$ are the same meanings as hereinbefore defined), or
(3) C1–6 alkyl which is substituted by C1–4 alkoxy; the other symbols are as defined in claim 1.
with the proviso that
(i) at least one group in $R^{7A}$, R8A and $R^{9A}$ represents C1–6 alkyl which is substituted by C1–4 alkoxy, and
(ii) when at least one group in $R^{7A}$, $R^{8A}$ and $R^{9A}$ contains t-butyl ester, the other groups do not represent groups containing carboxy;
or acid-addition salts thereof.

The compounds of the present invention represented by hereinafter formulae are desirable.

TABLE 1

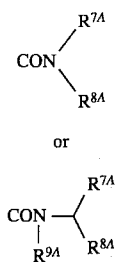

(I-X)

| | R$^S$ | R$^T$ | R$^U$ |
|---|---|---|---|
| 1 | ⁀COOEt | ⁀COOEt | ⁀⁀O⁀ |
| 2 | ⁀COOH | ⁀COOEt | ⁀⁀O⁀ |
| 3 | ⁀COOH | ⁀COOH | ⁀⁀O⁀ |
| 4 | ⁀COOEt | ⁀⁀COOEt | ⁀⁀O⁀ |
| 5 | ⁀COOEt | ⁀⁀COOH | ⁀⁀O⁀ |
| 6 | p-C6H4-COOEt | ⁀⁀COOEt | ⁀O⁀ |
| 7 | ⁀COOEt | =⁀COOEt | ⁀⁀O⁀ |
| 8 | ⁀⁀O⁀ | ⁀COOEt | ⁀COOEt |
| 9 | ⁀⁀O⁀ | ⁀COOEt | ⁀COOH |
| 10 | ⁀⁀O⁀ | ⁀COOH | ⁀COOH |

TABLE 1-continued (I-X) structure with R$^S$, R$^T$, R$^U$

| | R$^S$ | R$^T$ | R$^U$ |
|---|---|---|---|
| 11 | ⁀⁀O⁀ | ⁀⁀COOEt | ⁀COOEt |
| 12 | ⁀⁀O⁀ | ⁀⁀COOH | ⁀COOEt |

TABLE 2

(I-Y) structure with R$^S$, R$^T$

| | R$^S$ | R$^T$ |
|---|---|---|
| 1 | ⁀⁀O⁀ | ⁀COOEt |
| 2 | ⁀⁀O⁀ | ⁀COOH |
| 3 | ⁀⁀O⁀ | ⁀⁀COOEt |
| 4 | ⁀⁀O⁀ | ⁀⁀COOH |
| 5 | ⁀O⁀ | p-C6H4-COOEt |
| 6 | ⁀O⁀ | p-C6H4-COOH |
| 7 | ⁀⁀O⁀ | =⁀COOEt |
| 8 | ⁀⁀O⁀ | =⁀COOH |

TABLE 3

(I-Z) structure with R$^S$, R$^T$

| | R$^S$ | R$^T$ |
|---|---|---|
| 1 | ⁀⁀O⁀ | ⁀COOEt |
| 2 | ⁀⁀O⁀ | ⁀COOH |
| 3 | ⁀⁀O⁀ | ⁀⁀COOEt |

TABLE 3-continued (I-Z)

[Structure showing HN/H₂N-phenyl-O-C(=O)-phenyl-C(CH₃)=C(R^T)-C(=O)-N(R^S)(R^S)]

| | | | |
|---|---|---|---|
| 4 | ~~~O~ | ~~~COOH | |
| 5 | ~~O~ | phenyl-COOEt | |
| 6 | ~~O~ | phenyl-COOH | |
| 7 | ~~~O~ | =\COOEt | |
| 8 | ~~~O~ | =\COOH | |

Acid-Addition Salts

The compounds of the formula (I), of the present invention may be converted into the corresponding acid-addition salts by known methods. Non toxic and water-soluble salts are preferable. Suitable acid-addition salts include the salts with inorganic acids such as hydrochloric acid, hydrobromic acid, sulfuric acid, phosphoric acid and nitric acid, and the salts with organic acids such as acetic acid, trifluoroacetic acid, lactic acid, tartaric acid, oxalic acid, fumaric acid, maleic acid, citric acid, benzoic acid, methanesulfonic acid, ethanesulfonic acid, benzenesulfonic acid, toluenesulfonic acid, isethionic acid, glucuronic acid and gluconic acid.

Processes for the Preparation thereof

In the compounds of the formula (I), of the present invention, those in which all of $R^7$, $R^8$ and $R^9$, in $R^3$, represent groups not containing COOH and COOt—Bu, i.e., the compounds of the formula (Ia):

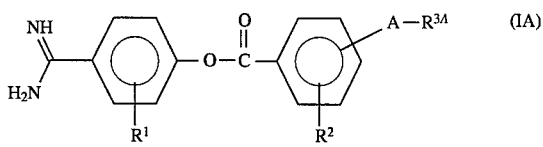
(IA)

wherein $R^1$, $R^2$ and A are the same meanings as hereinbefore defined, and $R^{3a}$ is the same meaning as hereinbefore defined for $R^3$, provided that all of $R^7$, $R^8$ and $R^9$, in $R^3$, are groups not containing COOH and COOt—Bu, may be prepared by esterification of a compound of the formula (IIa):

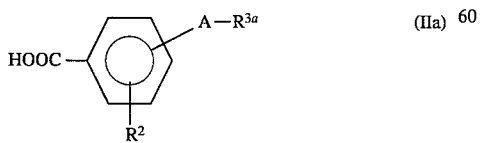
(IIa)

wherein $R^2$, $R^{3a}$ and A are the same meanings as hereinbefore defined, with a compound of the formula (III):

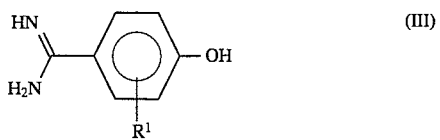
(III)

wherein $R^1$ is the same meaning as hereinbefore defined. The said esterification is known and can be carried out by methods for example:

(1) using an acid halide,
(2) using a mixed acid anhydride,
(3) using a condensing agent etc.

Each of these methods can be carried out, for example, as follows:

(1) the method using an acid halide may be carried out, for example, by reacting a carboxylic acid with an acid halide (e.g., oxalyl chloride, thionyl chloride etc.) in an inert organic solvent (e.g., chloroform, methylene chloride, diethyl ether, tetrahydrofuran etc.) or without a solvent at from −20° C. to the reflux temperature of the solvent, and then by reacting the acid halide obtained with a corresponding alcohol in the presence of a tertiary amine (e.g., pyridine, triethylamine, dimethylaniline, dimethylaminopyridine etc.) in an inert organic solvent (e.g., chloroform, methylene chloride, diethyl ether, tetrahydrofuran etc.), at a temperature of from 0° C. to 40° C., (2) the method using a mixed acid anhydride may be carried out, for example, by reacting a carboxylic acid and an acid halide (e.g., pivaloyl chloride, tosyl chloride, mesyl chloride etc.) or an acid derivative (e.g., ethyl chloroformate, isobutyl chloroformate etc.) in the presence of a tertiary amine (e.g., pyridine, triethylamine, dimethylaniline, dimethylaminopyridine etc.) in an inert organic solvent (e.g., chloroform, methylene chloride, diethyl ether, tetrahydrofuran etc.) or without a solvent at a temperature of from 0° C. to 40° C., and then by reacting the mixture of acid anhydride obtained with a corresponding alcohol in an inert organic solvent (e.g., chloroform, methylene chloride, diethyl ether, tetrahydrofuran etc.), at a temperature of from 0° C. to 40° C., (3) the method using a condensing agent (e.g., 1,3-dicyclohexyl carbodiimide (DCC), 1-ethyl-3-[ 3-(dimethylamino)propyl]carbodiimide(EDC), 2-chloro-1-methylpyridinium iodide etc.) may be carried out, for example, by reacting a carboxylic acid with a corresponding alcohol using a condensing agent in the presence or absence of a tertiary amine (e.g., pyridine, triethylamine, dimethylaniline, dimethylaminopyridine etc.) in an inert organic solvent (e.g., chloroform, methylene chloride, dimethyl formamide, diethyl ether etc.) or without a solvent at a temperature of from 0° C. to 40° C.

The reactions (1), (2) and (3) hereinbefore described may be preferably carried out in an atmosphere of inert gas (e.g., argon, nitrogen etc.) under anhydrous conditions.

In the compounds of the formula (I), those in which at least one group of $R^7$, $R^8$ and $R^9$ in $R^3$ represents a group containing COOt—Bu and the other groups represent ones not containing COOH, i.e., the compounds of the formula (Ib):

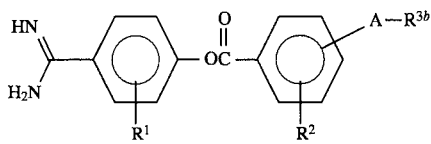

wherein $R^1$, $R^2$ and A have the same meanings as hereinbefore defined and $R^{3b}$ has the same meaning as hereinbefore defined for $R^3$, provided that at least one groups of $R^7$, $R^8$ and $R^9$, in $R^3$, is a group containing COOt—Bu and the other groups are ones not containing COOH, may be prepared by amidation of a compound of the formula (IIb):

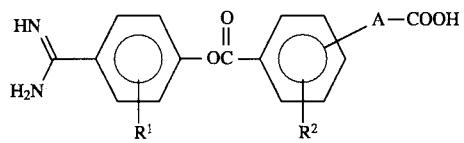

wherein the various symbols are the same meanings as hereinbefore defined, with a compound of the formula (IIIb):

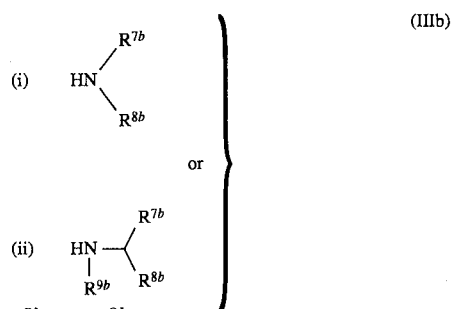

wherein $R^{7b}$, $R^{8b}$ and $R^{9b}$ are the same meanings as hereinbefore defined for $R^7$, $R^8$ and $R^9$, respectively, provided that at least one group of $R^{7b}$, $R^{8b}$ and $R^{9b}$ is a group containing COOt—Bu and the other groups are ones not containing COOH. The said amidation can be carried out, by the same condition as hereinbefore described for the esterification using an amine of the formula (IIIb) instead of an alcohol of the formula (III). In the compounds of the formula (I), those in which at least one group of $R^7$, $R^8$ and $R^9$, in $R^3$, represents a group containing COOH and the other groups represent ones not containing COOt—Bu, i.e., the compounds of the formula (Ic):

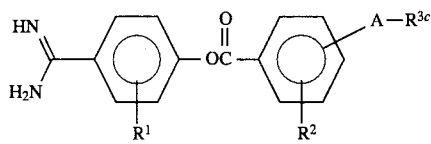

wherein $R^1$, $R^2$ and A have the same meanings as hereinbefore defined and $R^{3c}$ is the same meaning as hereinbefore defined for $R^3$, provided that at least one group of $R^7$, $R^8$ and $R^9$, in $R^3$, is a group containing COOH and the other groups are ones not containing COOt—Bu, may be prepared by the hydrolysis of t-butyl ester group, of a compound of the formula (Ib):

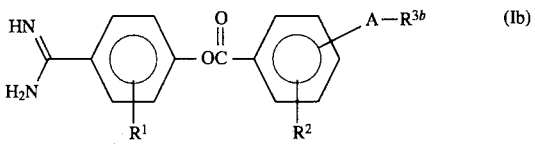

wherein the various symbols have the same meanings as hereinbefore defined. The hydrolysis of t-butyl ester group may be carried out, for example, by using an organic acid (e.g., trifluoroacetic acid etc.) or an inorganic acid (e.g., hydrochloric acid etc.), or the mixture thereof, in an inert organic solvent (e.g., methylene chloride, chloroform, methanol, dioxane, ethyl acetate, anisole etc.) at a temperature of from 0° C. to 90° C.

In the compounds of the formula (IIa), those in which all of $R^7$, $R^8$ and $R^9$, in $R^{3a}$, represent groups not containing benzyloxycarbonyl, allyloxycarbonyl and propargyloxycarbonyl, i.e., the compounds of the formula (IIa-1):

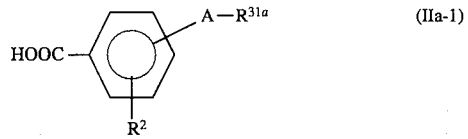

wherein $R^2$ and A are the same meanings as hereinbefore defined and $R^{31a}$ is the same meaning as hereinbefore defined for $R^{3a}$, provided that all of $R^7$, $R^8$ and $R^9$, in $R^{3a}$, are groups not containing benzyloxycarbonyl, allyloxycarbonyl and propargyloxycarbonyl, may be prepared by methods known per se, for example, by a series of reactions depicted in the following Scheme A.

In the Scheme A, $R^2$, A, and $R^{31a}$ are the same meanings as hereinbefore defined and $R^{71a}$, $R^{81a}$ and $R^{91a}$ are the same meanings as hereinbefore defined for $R^7$, $R^8$ and $R^9$, respectively, provided that all of $R^7$, $R^8$ and $R^9$ are groups not containing benzyloxycarbonyl, allyloxycarbonyl and propargyloxycarbonyl.

Scheme A

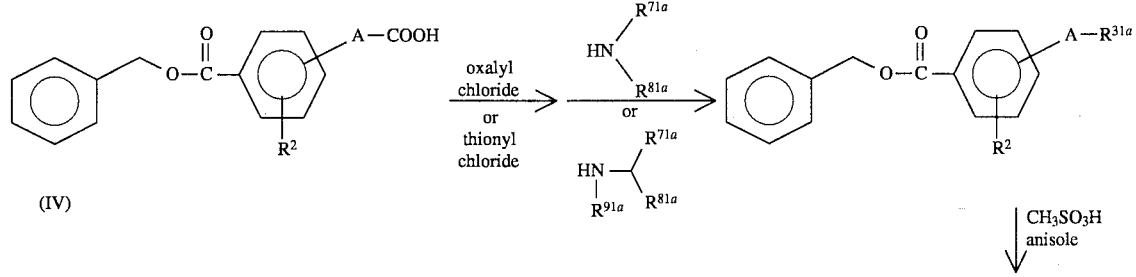

-continued
Scheme A

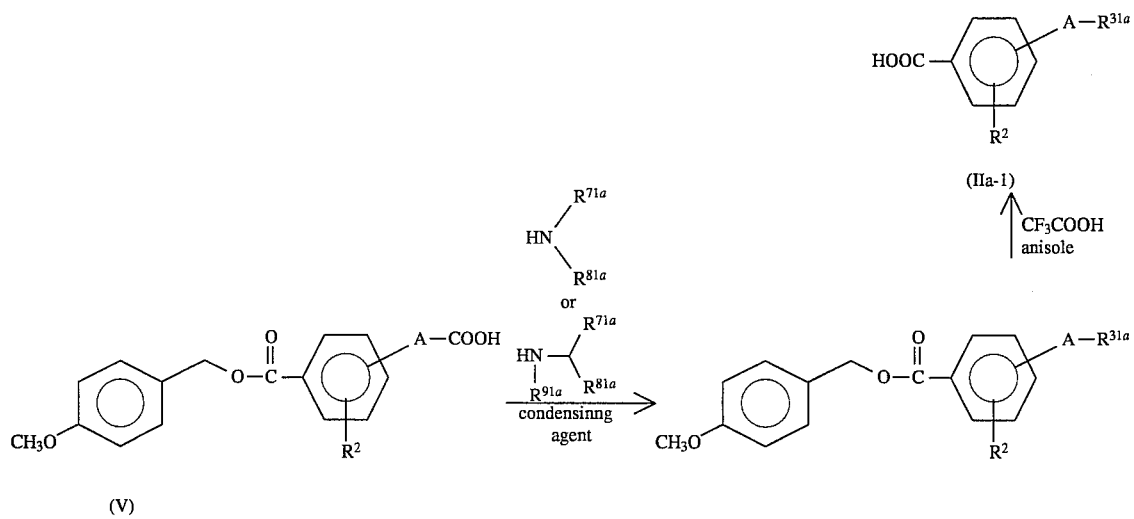

In the compounds of the formula (IIa), those in which at least one group of R7, R8 and R9, in $R^{3a}$, represents a group containing benzyloxycarbonyl, allyloxycarbonyl or propargyloxycarbonyl, i.e., the compounds of the formula (IIa-2):

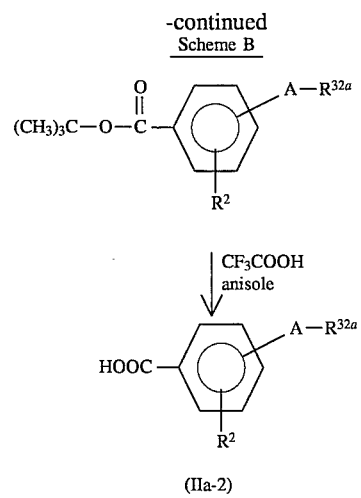

wherein $R^2$ and A have the same meanings as hereinbefore defined and $R^{32a}$ is the same meaning as hereinbefore defined for $R^{3a}$, provided that at least one group of $R^7$, $R^8$ and $R^9$, in $R^{3a}$, is a group containing benzyloxycarbonyl, allyloxycarbonyl and propargyloxycarbonyl, may be prepared by methods known per se, for example, by a series of reactions depicted in the following Scheme B.

in the Scheme B, $R^2$, A and $R^{32a}$ have the same meanings as hereinbefore defined and $R^{72a}$, $R^{82a}$ and $R^{92a}$ have the same meanings as hereinbefore defined for $R^7$, $R^8$ and $R^9$, respectively, provided that at least one group of $R^7$, $R^8$ and $R^9$ is a group containing benzyloxycarbonyl, allyloxycarbonyl or propargyloxycarbonyl.

Scheme B

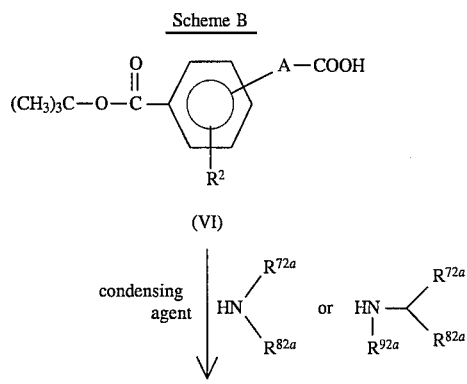

The compounds of the formula (IIb) may be prepared by methods known per se, for example, by a series of reactions depicted in the following Scheme C.

In the Scheme C, A, $R^1$ and $R^2$ are the same meanings as hereinbefore defined.

Scheme C

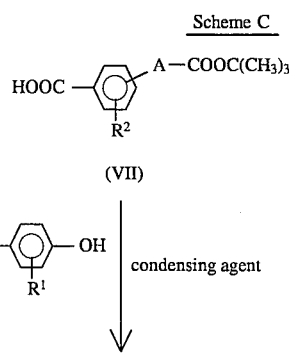

-continued
Scheme C

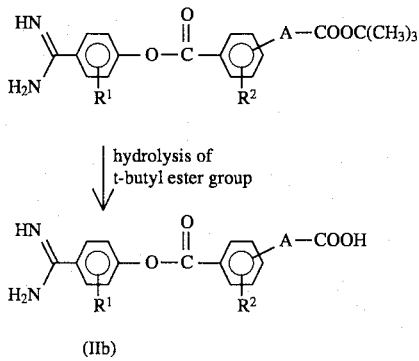

(IIb)

In the Scheme A, B and C, $CH_3SO_3H$ is methanesulfonic acid, $CF_3COOH$ is trifluoroacetic acid.

The reactions in schemes hereinbefore depicted may be carried out by methods known per se. The compounds of the formulae (IV), (V), (VI) and (VII) used as starting materials in the schemes hereinbefore depicted, are known per se or may be easily prepared by methods known per se.

In each reaction in the present specification, products may be purified by a conventional manner. For example, it may be carried out by distillation at atmospheric or reduced pressure, high performance liquid chromatography, thin layer chromatography or column chromatography using silica gel or magnesium silicate, washing or recrystallization. Purification may be carried out after each reaction, or after a series of reactions.

Other starting materials and reagents are known per se or may be prepared by known methods.

Pharmacological Activity

It has been confirmed that the compounds of the formula (I), of the present invention have inhibitory activities on $PLA_2$ and on various proteases such as trypsin, plasmin, thrombin, kallikrein. For example, in laboratory tests the following results were obtained.

Method (1) Inhibitory activity on $PLA_2$

A reaction solution including 50 mM tris-HCl buffer (pH7.5, 874 µl; containing 100 mM sodium chloride, 1 mM EDTA), 1M calcium chloride (6 µl), 1% bovine serum albumin (10 µl) and 2.5 mM 10PY-PC (10 µl), was prepared. To the solution were added solutions of a test compound in respective concentrations or water (50 µl), and a solution of 10 mU/ml $PLA_2$ (derived from hog pancreas) (50 µl). The appearance of fluorescence was measured (Ex=345 nm, Em=396 nm). Percentage of the strength of fluorescence in the presence of a test compound was calculated when the strength of that in the absence thereof was regarded as 100%, and therefrom $IC_{50}$ value was calculated. The results are shown in the following Table 4.

TABLE 4

| Inhibitory Activity on $PLA_2$ | |
| --- | --- |
| Compound (Example No. | $IC_{50}$ (µM) |
| 1 | 107 |
| 1(a) | 106 |
| 1(b) | 124 |

(2) Inhibitory activity on trypsin

To a mixture of a 0.2 M HEPES-sodium hydroxide buffer solution (pH 8.0, 100 µl) and distilled water (640 µl), were added solutions of a test compound in respective concentrations or water (10 µl), and a solution of 80 mU/ml trypsin (derived from bovine pancreas) (50 µl) and then the mixture was preincubated for one minute at 30° C. To the solution thus obtained was added 2.5 mM BAPNA (200 µl) and the mixture was incubated at 30° C. The absorbance at 405 nm was measured. Percentage (%) of the absorbance in the presence of a test compound was calculated when the absorbance in the absence thereof was regarded as 100%, and therefrom $IC_{50}$ value was calculated. The results are shown in the following Table 5.

TABLE 5

| Inhibitory Activity on trypsin | |
| --- | --- |
| Compound (Example No.) | $IC_{50}$ (µM) |
| 1 | 0.136 |
| 1(a) | 0.253 |
| 1(b) | 0.17 |
| 3 | 0.14 |

In the methods hereinbefore described, 10PY-PC represents 3'-palmitoyl-2-(1-opyrenedecanoyl)-L-α-phosphatidylcholine, HEPES represents 4-(2-hydroxyethyl)-1-piperazineethanesulfonic acid, and BAPNA represents α-N-benzoyl-DL-arginine-p-nitroanilide hydrochloride.

Toxicity

The toxicity of the compounds of the present invention is very low. Therefore, the compounds of the present invention may be considered to be sufficiently safe and suitable for pharmaceutical use.

Application for pharmaceuticals

The inhibition on $PLA_2$ and on various proteases such as trypsin, plasmin, thrombin, kallikrein, especially trypsin in animals including human beings, most especially in human beings, are useful for the prevention and/or the treatment of various inflammatory diseases, allergic diseases, disseminated intravascular coagulation, pancreatitis, severity in pancreatitis and multiple organ failure.

For the purpose hereinbefore described, the compounds of the formula (I), of the present invention, non-toxic acid addition salts thereof, or hydrates thereof may be normally administered systemically or partially, usually by oral or parenteral administration.

The doses to be administered are determined depending upon age, symptom, the desired therapeutic effect, the route of administration, and the duration of the treatment etc. In the human adult, the doses per person per dose are generally between 1 mg and 1000 mg, by oral administration, up to several times per day, and between 1 mg and 100 mg, by parenteral administration (preferably, intravenously) up to several times per day, or continuous administration between 1 and 24 hrs. per day through a vein.

As mentioned above, the doses to be used depend upon various conditions. Therefore, there are cases in which doses lower than or greater than the ranges specified above may be used.

When administering the compounds of the present invention, it is used in the form of solid compositions, liquid compositions or other compositions for oral administration, as injections, liniments or suppositories etc. for parenteral administration.

Solid compositions for oral administration include compressed tablets, pills, capsules, dispersible powders, and granules.

Capsules include hard capsules and soft capsules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate, etc.). The compositions may also comprise, as in normal practice, additional substances other than inert diluents: e.g. lubricating agents (such as magnesium stearate, etc.), disintegrating agents (such as cellulose calcium glycolate, etc.), stabilizing agents (such as lactose, etc.), and assisting agents for dissolving (such as glutamic acid, asparaginic acid etc.). The tablets or pills may, if desired, be coated with a film of gastric or enteric material (such as sugar, gelatin, hydroxypropyl cellulose or hydroxypropylmethyl cellulose phtalate etc.), or be coated with more than two films. And further, coating may include containment within capsules of absorbable materials such as gelatin.

Liquid compositions for oral administration include pharmaceutically-acceptable emulsions, solutions, syrups and elixirs. The compositions may also comprise inert diluents commonly used in the art (purified water, ethanol etc.). Besides inert diluents, such compositions may also comprise adjuvants (such as wetting agents, suspending agents, etc.), sweetening agents, flavoring agents, perfuming agents, and preserving agents.

Other compositions for oral administration include spray compositions which may be prepared by known methods and which comprise one or more of the active compound(s). Spray compositions may comprise additional substances other than inert diluents: e.g. stabilizing agents (sodium sulfate etc.), isotonic buffer (sodium chloride, sodium citrate, citric acid, etc.). For preparation of such spray compositions, for example, the method described in the U.S. Pat. No. 2,868,691 or 3,095,355 (herein incorporated in their entireties by reference) may be used.

Injections for parenteral administration include sterile aqueous or non-aqueous solutions, suspensions and emulsions. In such compositions, one more of active compound(s) is or are admixed with at least one of inert aqueous diluent(s) (distilled water for injection, physiological salt solution etc.) or inert non-aqueous diluent(s) (propylene glycol, polyethylene glycol, plant oils such as olive oil, alcohols such as ethanol, POLYSORBATE 80®, etc.). Injections may comprise additional other than inert diluents: e.g. preserving agents, wetting agents, emulsifying agents, dispersing agents, stabilizing agent (lactose etc.), assisting agents such as assisting agents for dissolving (glutamic acid, asparaginic acid etc.). They may be sterilized for example, by filtration through a bacteria-retaining filter, by incorporation of sterilizing agents in the compositions or by irradiation. They may also be manufactured in the form of sterile solid compositions, for example, by freeze-drying, which may be dissolved in sterile water or some other sterile diluent(s) for injection immediately before use.

Other compositions for parenteral administration include endermic ones such as liquids for external use, ointment, and endermic liniments, and suppositories and pessaries for intrarectal administration which comprise one or more of the active compound(s) and may be prepared by per se known methods.

Examples

The following reference examples and examples illustrate, but do not limit, the present invention.

The solvents in parentheses show the developing or eluting solvents and the ratios of the solvents used are by volume in chromatographic separations.

Unless otherwise specified "IR" was measured by KBr method, and "NMR" was measured in a solution of deuteromethanol.

Reference Example 1 p-Benzyloxycarbonyl-α-methylcinnamic acid t-butyl ester

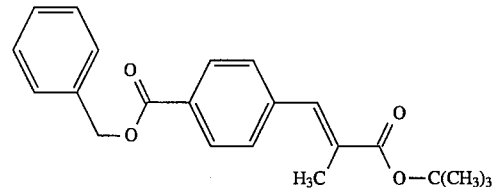

To a suspension of sodium hydride (0.8 g, containing 60% oil) in tetrahydrofuran (25 ml) was added slowly dropwise a solution of 2-(diethylphosphono)propionic acid t-butyl ester (4.8 g) in tetrahydrofuran (6 ml) under cooling with ice, and the mixture was stirred for 30 min. at room temperature. After the reaction mixture was cooled with ice, a solution of p-benzyloxycarbonylbenzaldehyde (4.0 g) in tetrahydrofuran (15 ml) was added slowly dropwise thereto. The mixture was stirred for 30 min. at room temperature, water was added thereto, and then the reaction mixture was extracted with ethyl acetate. The extract was washed with water, a saturated aqueous solution of sodium bicarbonate and a saturated aqueous solution of sodium chloride, successively, dried over anhydrous magnesium sulfate, and evaporated. The residue was purified by silica gel column chromatography (hexane: ethyl acetate=20:1→15:1) to give the title compound (5.2 g) having the following physical data:

TLC: Rf 0.34 (hexane: ethyl acetate=10:1).

Reference Example 2 p-Benzyloxycarbonyl-α-methylcinnamic acid

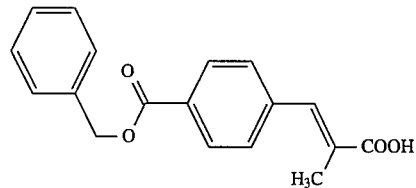

To a solution of the compound prepared in Reference Example 1 (56.0 g) in anisole (40 ml) was added trifluoroacetic acid (75 ml) under cooling with ice. After being stirred for two hours at room temperature, the reaction mixture was concentrated under reduced pressure to obtain a white solid. The thus-obtained white solid was washed with isopropyl ether, filtered, and dried under reduced pressure to give the title compound (39.57 g) as white crystal having the following physical data:

TLC: Rf 0.26 (hexane: ethyl acetate: acetic acid=12:4:1).

Reference Example 3 p-(Benzyloxycarbonyl)-α-methylcinnamic acid N-2-ethoxycarbonylethyl-N-3-methoxypropylamide

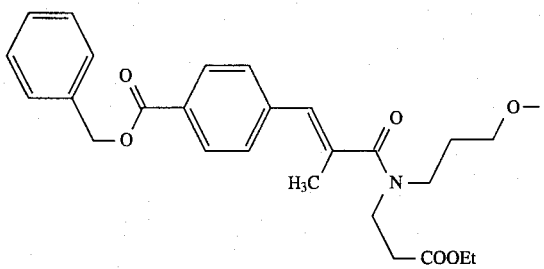

To a solution of the compound prepared in Reference Example 2 (5.58 g) was added thionyl chloride (40 ml) at room temperature. The reaction mixture was stirred for one hour at 120° C. After being cooled to room temperature, the reaction mixture was concentrated under reduced pressure. To a solution of N-2-ethoxycarbonylethyl-N-3-methoxypropylamine (3.56 g) in methylene chloride (20 ml) and pyridine (20 ml) was added slowly dropwise a solution of obtained acid chloride in methylene chloride (20 ml). The reaction mixture was stirred for one hour at room temperature and concentrated under reduced pressure. The residue was diluted with ethyl acetate and poured into a solution of 1 N hydrochloric acid cooled with ice, and the mixture was separated into two layers. The organic layer was washed with water, a saturated aqueous solution of sodium bicarbonate and a saturated aqueous solution of sodium chloride, successively, dried over anhydrous magnesium sulfate, and evaporated to give the title compound (5.24 g) having the following physical data:

TLC: Rf 0.47 (hexane: ethyl acetate=1:2).

Reference Example 4 p-Carboxy-α-methylcinnamic acid N-2-ethoxycarbonylethyl-N-3-methoxypropylamide

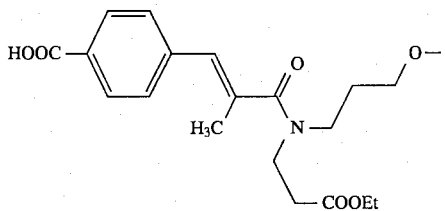

To a solution of the compound prepared in Reference Example 3 (5.24 g) in anisole (44 ml), was added methanesulfonic acid (22 ml) at room temperature. The reaction mixture was stirred for two hours at room temperature and concentrated under reduced pressure. To the residue was added ice water and ether, and the mixture was separated into two layers. The organic layer was washed with water and extracted with a saturated aqueous solution of sodium bicarbonate. All aqueous layers were collected and were acidified by addition of 1N hydrochloric acid under cooling with ice, and then extracted with ethyl acetate. The extract was washed with water and a saturated aqueous solution of sodium chloride, successively, dried over anhydrous magnesium sulfate, and evaporated. The residue was purified by silica gel column chromatography (chloroform: methanol= 100:1→ 50:1) to give the title compound (4.2 g) having the following physical data:

TLC: Rf 0.30 (chloroform: methanol=9:1).

Example 1 p-(p-Amidinophenoxycarbonyl)-α-methylcinnamic acid N-2-ethoxycarbonylethyl-N-3-methoxypropylamide hydrochloride

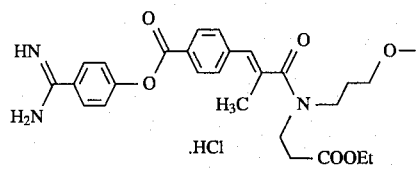

To a solution of the compound prepared in Reference Example 4 (4.20 g) in pyridine (30 ml), were added successively p-amidinophenol hydrochloride (1.92 g) and 1,3-dicyclohexylcarbodiimide (3.45 g). After being stirred overnight at room temperature, the reaction mixture was filtered. The filtrate was evaporated. The residue was purified by silica gel column chromatography (chloroform: methanol: acetic acid=50:5:1→ 30:3:1) to give the title compound (1.81 g) as white powder having the following physical data:

TLC: Rf 0.60 (chloroform: methanol: acetic acid=10:2:1); IR: ν3424, 1736, 1677, 1606, 1478, 1267, 1217, 1177, 1115, 1067, 1015 cm$^{-1}$; NMR: δ8.20 (2H, d, J=8Hz), 7.95 (2H, d, J=9Hz), 7.60–7.50 (4H, m), 6.60 (1 H, br.), 4.15 (2H, q, J=7Hz), 3.75 (2H, m), 3.55 (2H, m), 3.45 (2H m), 3.30 (3H, m), 2.70 (2H, t, J=6.5Hz), 2.15 (3H, s), 1.95 (2H, m), 1.25 (3H, t, J=7Hz).

Example 1(a)–(c)

By the same procedure as a series of reactions of Reference Example 3→Reference Example 4→Example 1, using, as starting materials, the compound prepared in Reference Example 2, and using other amines instead of N-2-ethoxycarbonylethyl-N-3-methoxypropylamine,the compounds of the present invention shown as follows were given:

Example 1 (a)

p-(p-Amidinophenoxycarbonyl)-α-methylcinnamic acid N-ethoxycarbonylethyl-N-3-methoxypropylamide acetate

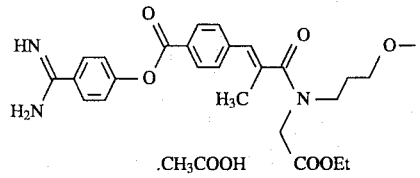

TLC: Rf 0.24 (chloroform: methanol: acetic acid=10:2:1); IR: ν3257, 2982, 1741, 1673, 1608, 1479, 1409, 1264, 1211, 1176, 1118, 1060, 1011, 883, 740 cm$^{-1}$; NMR: δ8.21 (2H, d, J=8Hz), 7.92 (2H, d, J=8Hz), 7.57 (4H, t, J=8Hz), 6.61 and 6.70 (1 H, s), 4.1–4.3 (4H, m), 3.5–3.7 (2H, m), 3.4–3.5 (2H, 3.2–3.4 (3H, m), 2.09 and 2.12 (3H, s), 1.91 (3H, s), 1.8–2.0 (2H, m), 1.29 (3H, t, J=7Hz).

Example 1 (b) p-(p-Amidinophenoxycarbonyl)-α-methylcinnamic acid N-1,1-bis(ethoxycarbonyl)methyl-N-3-methoxypropylamide acetate

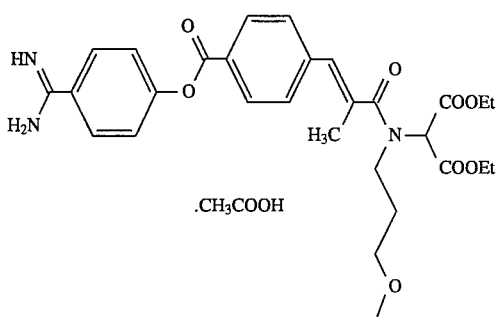

TLC: Rf 0.34 (chloroform: methanol: acetic acid=10:2:1); IR:ν3204, 2984, 1737, 1607, 1484, 1412, 1267, 1212, 1177, 1117, 1069, 1015, 888, 740 cm$^{-1}$; NMR: δ8.23 (2H, d, J=8Hz), 7.92 (2H, d, J =8Hz), 7.58 (2H, d, J=8Hz), 7.53 (2H, d, J=8Hz), 6.59 and 6.70 (1 H, s), 4.8–4.9 (1 H, m), 4.27 (4H, q J=7Hz), 3.55–3.70 (2H, br), 3.43 (2H, t, J=7Hz), 3.26 (3H, s), 2.16 (3H, s), 1.92 (3H, s), 1.30 (6H, t, J=7Hz).

Example 1 (c)

p-(p-Amidinophenoxycarbonyl)-α-methylcinnamic acid N-ethoxycarbonylethyl-N-2-methoxyethylamide acetate

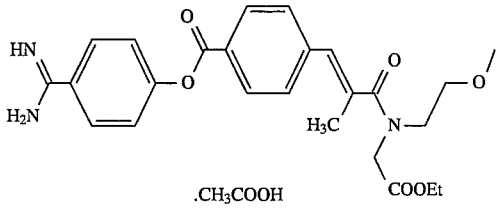

TLC: Rf 0.41 (chloroform: methanol: acetic acid=10:2:1);

To a solution of the compound prepared in Reference Example 5 (8.1 g) in ethanol (60 ml) was added 5N aqueous solution of sodium hydroxide (6 ml) under cooling with ice. After stirred overnight at room temperature, the reaction mixture was quenched by addition of 2N hydrochloric acid (15 ml), and then evaporated till the volume of the solution became ½. An aqueous solution thus obtained was extracted with ethyl acetate. The extract was washed with a saturated aqueous solution of sodium chloride, dried over anhydrous magnesium sulfate and evaporated to give the title compound (7.3 g) having the following physical data:

TLC:Rf 0.42 (ethyl acetate).

Reference Example 7 p-(p-Amidinophenoxycarbonyl)-α-methylcinnamic acid t-butyl ester

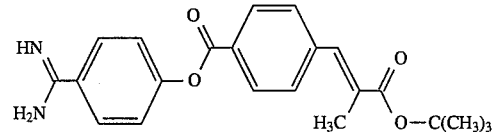

By the same procedure as Example 1, using the compound prepared in Reference Example 6, the title compound having the following physical data was given:

TLC: Rf 0.41 (chloroform: methanol: acetic acid=10:2:1). IR:ν3187, 2980, 1741, 1673, 1610, 1467, 1408, 1265, 1211, 1174, 1118, 1059, 1012, 880, 741 cm$^{-1}$; NMR: δ8.21 (2H, d, J=8Hz), 7.92 (2H, d, J=8Hz), 7.65–7.50 (4H, m), 6.72 and 6.65 (1 H, s, rotamer), 4.2–4.1 (4H, m), 3.8–3.6 (2H, br), 3.6–3.5 (2H, br), 3.34 (3H, s), 2.17 (3H, s), 1.91 (AcOH), 1.35–1.15 (3H, br).

Reference Example 5 p-Methoxycarbonyl-α-methylcinnamic acid t-butyl ester

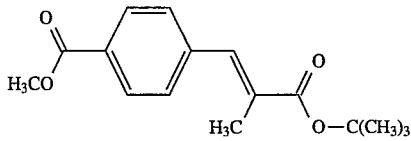

By the same procedure as Reference Example 1, using p-methoxycarbonyl benzaldehyde instead of benzyloxycarbonyl benzaldehyde, the title compound having the following physical data was given:

TLC: Rf 0.67 (hexane: ethyl acetate=4:1).

Reference Example 6 p-Carboxyl-α-methylcinnamic acid t-butyl ester

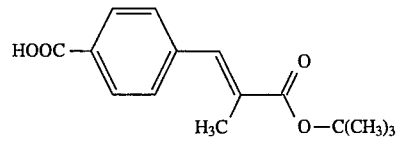

Reference Example 8 p-(p-Amidinophenoxycarbonyl)-α-methylcinnamic acid hydrochloride

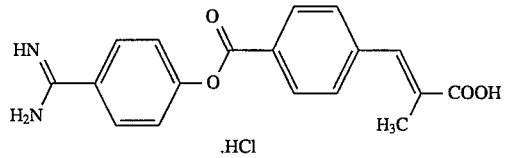

To a solution of the compound prepared in Reference Example 7 (4.79 g) in chloroform (100 ml), were added successively a solution of 4N hydrochloric acid in ethyl acetate (50 ml) and dioxane (10 ml). The mixture was stirred for two hours at room temperature and evaporated. The residue thus obtained was washed with ether, filtered and then dried to give the title compound (4.15 g) having the following physical data:

TLC: Rf 0.38 (chloroform: methanol: acetic acid=10:2:1); NMR: δ8.21 (2H, d, J=8.0Hz), 7.95 (2H, d, J=8.0Hz), 7.75 (1 H, s), 7.60 (2H, d, J=8.0Hz), 7.54 (2H, d, J=8.0Hz), 2.12 (3H, s).

Example 2 p-(p-Amidinophenoxycarbonyl)-α-methylcinnamic acid N-t-butoxycarbonylmethyl-N-3-methoxypropylamide hydrochloride

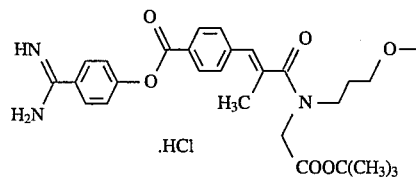

To a suspension of the compound prepared in Reference Example 8 (3.2 g) in a mixture of pyridine (50 ml) and dimethylformamide (5 ml), were added successively a solution of N-t-butoxycarbonylmethyl-N-3-methoxypropylamine (1.52 g) in pyridine (5 ml) and a solution of 1,3-dicyclohexylcarbodiimide (2.20 g) in pyridine (5 ml). The mixture was stirred overnight at room temperature and evaporated. The residue thus obtained was purified by silica gel column chromatography (chloroform: methanol: acetic acid=80: 2:1→40:2:1→20:2:1) to give the title compound (683 mg) having the following physical data:

TLC: Rf 0.25 (chloroform: methanol: acetic acid=20:2:1); NMR: δ8.21 (2H, d, J=8Hz), 7.91 (2H, d, J=8Hz), 7.65–7.50 (4H, m), 6.70–6.60 (1H, m), 4.20–4.00 (2H, m), 3.70–3.30 (4H, m), 2.20–2.05 (3H, m), 1.95 (3H, s), 2.00–1.80 (2H, m), 1.50–1.40 (9H, m).

Example 3 p-(p-Amidinophenoxycarbonyl)-α-methylcinnamic acid N-carboxylmethyl-N-3-methoxypropylamide methanesulfonate

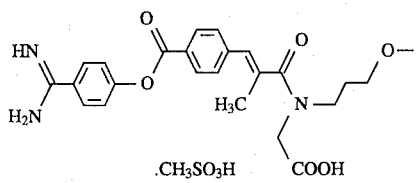

To a solution of the compound prepared in Example 2 (683 mg) was added trifluoroacetic acid (6.5 ml) at room temperature. The reaction mixture was stirred for one hour and evaporated. To the residue was added ether, and the mixture was crystallized to give the title compound trifluoroacetate. To the obtained trifluoroacetate in acetic acid (8 ml) was added methanesulfonic acid (0.1 ml) at room temperature. The reaction mixture was stirred for 30 min. at room temperature and evaporated. A solution of the residue in water (5 ml) was freeze-dried to give the title compound (286 mg) having the following physical data:

TLC: Rf 0.13 (chloroform: methanol: acetic acid=20:2:1); IR: ν3500–2700, 1742, 1693, 1606, 1482, 1206, 1062, 1016, 891, 789, 537 cm$^{-1}$; NMR: δ8.25–8.12 (2H, m), 7.90 (2H, d, J=8Hz), 7.60–7.45 (4H, m), 6.71 (1 H, bs), 4.03 (2H, s), 3.70–3.25 (7H, m), 2.70 (3H, s), 2.17–2.05 (3H, m), 2.00–1.80 (2H, m).

Formulation Example

Formulation Example 1

The following components were admixed in a conventional manner and punched out to obtain 100 tablets each containing 50 mg of active ingredient.

| | |
|---|---|
| p-(p-Amidinophenoxycarbonyl)-α-methylcinnamic acid N-carboxylmethyl-N-3-ethoxypropylamide methanesulfonate | 5.0 g |
| Carboxymethylcellulose calcium (disintegrating agent) | 0.2 g |
| Magnesium stearate (lubricating agent) | 0.1 g |
| Microcrystalline cellulose | 4.7 g |

Formulation example 2

The following components were admixed in a conventional manner. The solution was sterilized in a conventional manner, placed 5 ml portion into ampoules and freeze-dried to obtain 100 ampoules each containing 20 mg of the active ingredient.

| | |
|---|---|
| p-(p-Amidinophenoxycarbonyl)-α-methylcinnamic acid N-carboxymethyl-N-3-ethoxypropylamide methanesulfonate | 2.00 g |
| mannitol | 20 g |
| Distilled water | 1000 ml |

What we claim is:

1. A compound of the formula (I):

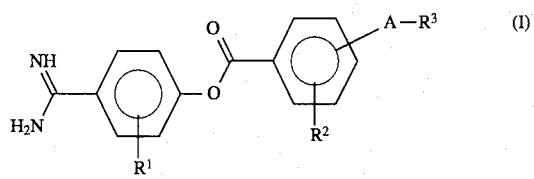

wherein $R^1$ and $R^2$ each, independently, is:
(i) hydrogen,
(ii) C1–4 alkyl,
(iii) C1–4 alkoxy,
(iv) C2–5 acyl,
(v) halogen,
(vi) nitro,
(vii) benzoyl, or
(viii) $COOR^4$ (in which $R^4$ is C1–3 alkyl);
A is bond, C1–4 alkylene, or $$-\underset{R^5}{\overset{}{C}}=\underset{R^6}{\overset{}{C}}-$$

in which $R^5$ and $R^6$ each, independently, is hydrogen or C1–4 alkyl;
$R^3$ is

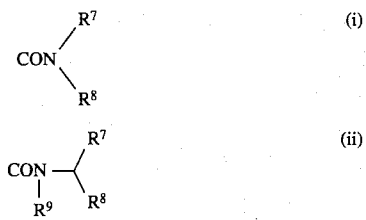

in which $R^7$ and $R^8$ each, independently, is
(1) hydrogen,
(2) phenyl,
(3) C7–10 phenylalkyl,
(4) phenyl or C7–10 phenylalkyl each of which is substituted by one or two substituents selected from C1–4 alkyl, halogen and $R^{11}$—$COOR^{12}$
in which $R^{11}$ is a
[1] bond,
[2] C1–8 alkylene,
[3] C2–8 alkenylene, or
[4] C2–8 alkynylene;
$R^{12}$ is
[1] hydrogen,
[2] C1–4 alkyl,
[3] C7–10 phenylalkyl,
[4] phenyl,
[5] allyl, or
[6] propargyl,
(5) C1–10 alkyl,
(6) C2–10 alkenyl having one to three double bonds,
(7) C2–10 alkynyl having one or two triple bonds,
(8) $R^{11a}$—$COXR^{12}$
in which $R^{11a}$ is a
[1] bond,
[2] C1–8 alkylene,
[3] C2–8 alkylene in which one or two carbon atoms in the main chain are replaced by sulfur, or sulfur and phenylene,
[4] C2–8 alkenylene,

[5] C4–8 alkenylene in which one or two carbon atoms in the main chain are replaced by sulfur, or sulfur and phenylene,

[6] C2–8 alkynylene, or

[7] C4–8 alkynylene in which one or two carbon atoms in the main chain are replaced by sulfur, or sulfur and phenylene, X is oxygen or —NH—, and $R^{12}$ has the same meaning as hereinbefore defined, (9) C1–4 alkyl which is substituted by a 7–14 membered, bi- or tri-cyclic hetero ring containing one nitrogen,

(10) C3–7 cycloalkyl, or

(11) C1–6 alkyl which is substituted by C1–4 alkoxy;

$R^9$ is (1) hydrogen, (2) C1–8 alkyl, (3) C7–10 phenylalkyl, (4) C2–10 alkenyl having one to three double bonds, (5) C2–10 alkynyl having one or two triple bonds, (6) $R^{11}$—$COOR^{12}$ in which $R^{11}$ and $R^{12}$ have the same meaning as hereinbefore defined, (7) C3–7 cycloalkyl, or (8) C1–6 alkyl which is substituted by C1–4 alkoxy; with the proviso that (i) at least one group in $R^7$, $R^8$ and $R^9$ represents C1–6 alkyl which is substituted by C1–4 alkoxy, (ii) both $R^7$ and $R^8$ do not represent hydrogen at the same time, and (iii) when at least one group in $R^7$, $R^8$ and $R^9$ represents groups containing t-butyl ester, the other groups in $R^7$, $R^8$ and $R^9$ do not represent groups containing carboxy;

or acid-addition salts thereof.

2. A compound according to claim 1, wherein the compound has the formula (I-A):

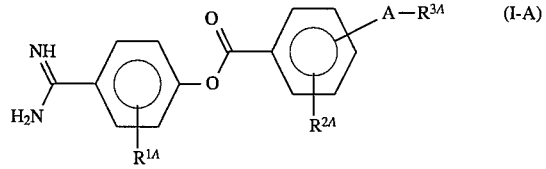

wherein $R^{1A}$ and $R^{2A}$ are the same meaning as defined for $R^1$ and $R^2$ in claim 1, respectively;

$R^{3A}$ is

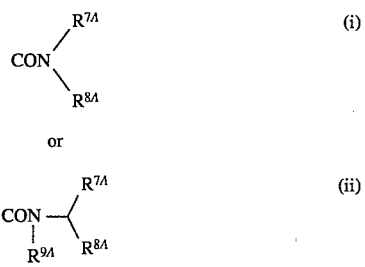

in which $R^{7A}$ and $R^{8A}$ each, independently, is (1) phenyl or C7–10 phenylalkyl each of which is substituted by one or two substituents selected from $R^{11}$—$COOR^{12}$ wherein $R^{11}$ and $R^{12}$ are as defined in claim 1, (2) $R^{11a}$—$COXR^{12}$ wherein $R^{11a}$, $R^{12}$ and X are as defined in claim 1, or (3) C1–6 alkyl which is substituted by C1–4 alkoxy;

$R^{9A}$ is (1) hydrogen, (2) $R^{11}$—$COOR^{12}$ wherein $R^{11}$ and $R^{12}$ are as defined in claim 1, or (3) C1–6 alkyl which is substituted by C1–4 alkoxy;

the other symbols are as defined in claim 1, with the proviso that (i) at least one group in $R^{7A}$, $R^{8A}$ and $R^{9A}$ represents C1–6 alkyl which is substituted by C1–4 alkoxy, and (ii) when at least one group in $R^{7A}$, $R^{8A}$ and $R^{9A}$ represents groups containing t-butyl ester, the other groups in $R^{7A}$, $R^{8A}$ and $R^{9A}$ do not represent groups containing carboxy;

or acid-addition salts thereof.

3. A compound according to claim 1, which is an acid-addition salt.

4. A compound according to claim 1, wherein $R^3$ is

in which $R^7$ and $R^8$ are as defined in claim 1.

5. A compound according to claim 1, wherein $R^3$ is

in which $R^7$, $R^8$ and $R^9$ are as defined in claim 1.

6. A compound according to claim 1, wherein one of $R^7$ and $R^8$ is (1) $R^{11a}$—$COXR^{12}$ wherein $R^{11a}$, $R^{12}$ and X are as defined in claim 1, or (2) C1–6 alkyl which is substituted by C1–4 alkoxy;

$R^9$ is (1) $R^{11}$—$COOR^{12}$ wherein $R^{11}$ and $R^{12}$ are as defined in claim 1, or (2) C1–6 alkyl which is substituted by C1–4 alkoxy.

7. A compound according to claim 1, which is p-(p-Amidinophenoxycarbonyl)-α-methylcinnamic acid N-2-ethoxycarbonylethyl-N- 3-methoxypropylamide, p-(p-Amidinophenoxycarbonyl)-α-methylcinnamic acid N-ethoxycarbonylethyl-N- 3-methoxypropylamide, p-(p-Amidinophenoxycarbonyl)-α-methylcinnamic acid N-1,1-bis(ethoxycarbonyl)methyl-N- 3-methoxypropylamide, p-(p-Amidinophenoxycarbonyl)-α-methylcinnamic acid N-t-butoxycarbonylmethyl-N- 3-methoxypropylamide, p-(p-Amidinophenoxycarbonyl)-α-methylcinnamic acid N-carboxylmethyl-N- 3-methoxypropylamide, or p-(p-Amidinophenoxycarbonyl)-α-methylcinnamic acid N-ethoxycarbonylmethyl-N- 2-methoxyethylamide.

8. A compound according to claim 1, wherein one of $R^7$ and $R^8$ is $R^{11}$—$COXR^{12}$ wherein $R^{11a}$, $R^{12}$ and X are as defined in claim 1; or (2) C1–6 alkyl which is substituted by C1–4 alkoxy.

9. A compound according to claim 1, wherein $R^9$ is $R^{11}$—$COOR^{12}$ wherein $R^{11}$ and $R^{12}$ are as defined in claim 1, or (2) C1–6 alkyl which is substituted by C1–4 alkoxy.

10. A method for the prevention and/or treatment in animals of various inflammatory diseases, allergic diseases, disseminated intravascular coagulation, pancreatitis, severity in pancreatitis or multiple organ failure, which comprises the administration to a patient of an effective amount of a compound of the formula (I) depicted in claim 1, or an acid addition salt thereof.

11. A method according to claim 10, wherein the animal is a human.

12. A pharmaceutical composition which comprises, as active ingredient, an effective amount of a compound of the formula (I) depicted in claim 1, or an acid addition salt thereof, with a carrier or coating.

* * * * *